（12） United States Patent
Lopez Villaverde et al.

(10) Patent No.: US 11,054,401 B2
(45) Date of Patent: Jul. 6, 2021

(54) METHOD FOR PROCESSING SIGNALS COMING FROM AN ACQUISITION BY ULTRASOUND PROBING, CORRESPONDING COMPUTER PROGRAM AND ULTRASOUND PROBING DEVICE

(71) Applicants: Commissariat a l'energie atomique et aux energies alternatives, Paris (FR); Centre National de la Recherche Scientifique, Paris (FR)

(72) Inventors: Eduardo-Rigoberto Lopez Villaverde, Massy (FR); Sebastien Robert, Le Kremlin-Bicetre (FR); Claire Prada Julia, Paris (FR)

(73) Assignees: Commissariat a l'energie atomique et aux energies alternatives, Paris (FR); Centre National de la Recherche Scientifique, Paris (FR)

( * ) Notice: Subject to any disclaimer, the term of this patent is extended or adjusted under 35 U.S.C. 154(b) by 35 days.

(21) Appl. No.: 16/469,918

(22) PCT Filed: Dec. 5, 2017

(86) PCT No.: PCT/FR2017/053391
§ 371 (c)(1),
(2) Date: Jun. 14, 2019

(87) PCT Pub. No.: WO2018/109314
PCT Pub. Date: Jun. 21, 2018

(65) Prior Publication Data
US 2019/0317054 A1   Oct. 17, 2019

(30) Foreign Application Priority Data

Dec. 15, 2016   (FR) ..................................... 16 62525

(51) Int. Cl.
*G06K 9/00*   (2006.01)
*G01N 29/44*   (2006.01)
(Continued)

(52) U.S. Cl.
CPC .......... *G01N 29/4463* (2013.01); *A61B 8/14* (2013.01); *A61B 8/5269* (2013.01); *A61B 8/54* (2013.01);
(Continued)

(58) Field of Classification Search
None
See application file for complete search history.

(56) References Cited

U.S. PATENT DOCUMENTS 9,903,842 B2 * 2/2018 Bannouf ................ G01N 29/24
10,386,335 B2 * 8/2019 Robert ................ G01S 15/8915
(Continued)

FOREIGN PATENT DOCUMENTS

| WO | WO 2010/142927 A1 | 12/2010 |
| WO | WO 2014/009671 A1 | 1/2014 |
| WO | WO 2015/092250 A1 | 6/2015 |

OTHER PUBLICATIONS

International Search Report dated Apr. 23, 2018 in PCT/FR2017/053391 filed on Dec. 5, 2017.
(Continued)

*Primary Examiner* — Soo Jin Park
(74) *Attorney, Agent, or Firm* — Oblon, McClelland, Maier & Neustadt, L.L.P.

(57) ABSTRACT

A method for processing ultrasound signals including controlling emission transducers for M successive emissions of plane ultrasound waves having M different angles of emission, controlling N reception transducers in order to simultaneously receive N measurement time signals per emission, and obtaining a matrix [MR(t)] of ultrasound time signals, each coefficient $MR_{i,j}(t)$ of this matrix representing the measurement signal received by the i-th reception transducer caused by the j-th emission. It further includes performing singular-value decomposition of a matrix [FTMR(f)] of
(Continued)

Figure 1:
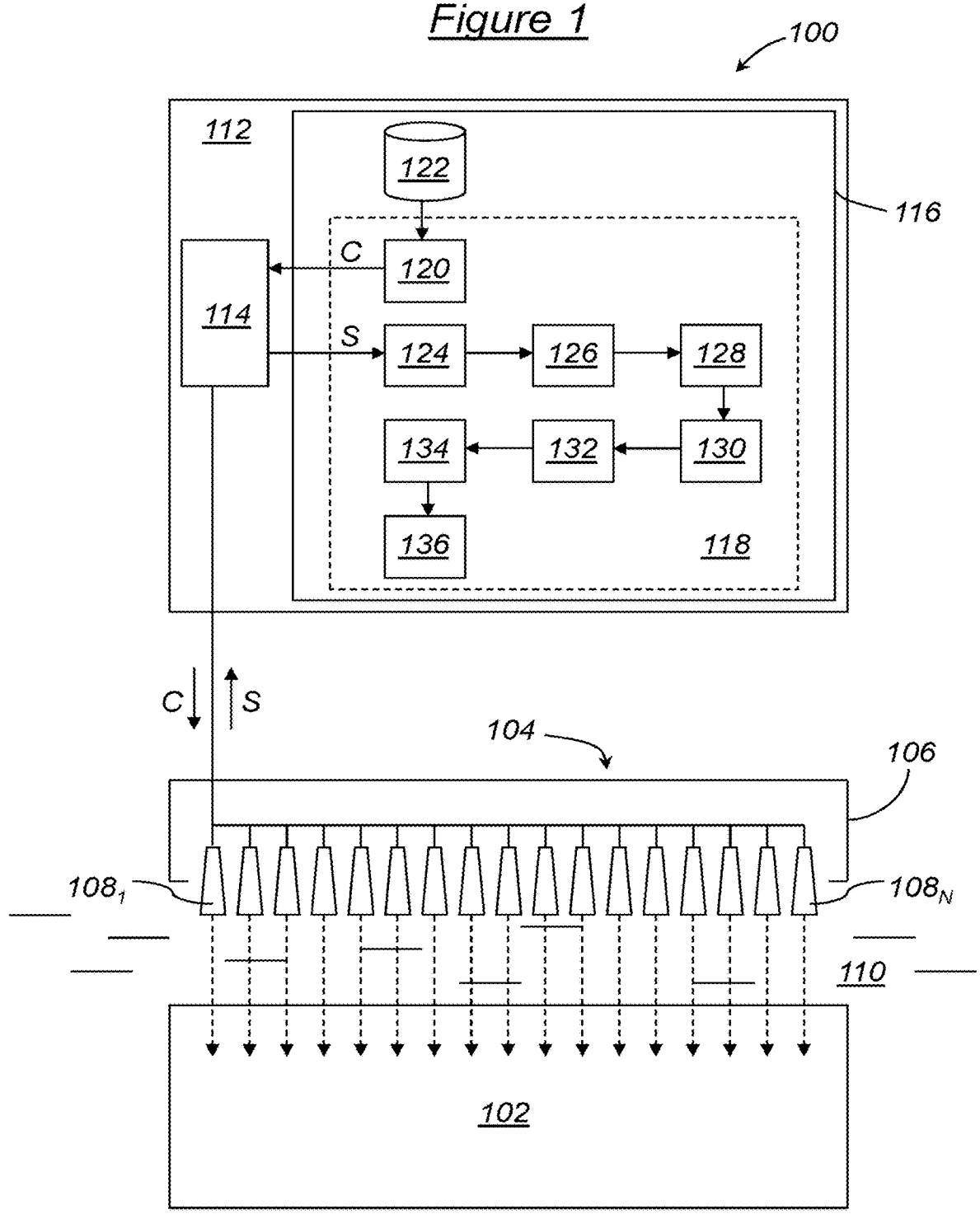

frequency signals obtained by transforming the matrix [MR(t)], and eliminating a portion of the singular values and reconstructing a denoised matrix [MR$_U$(t)] of time signals on the basis of the singular values not eliminated.

11 Claims, 4 Drawing Sheets

(51) Int. Cl.
      *A61B 8/14*       (2006.01)
      *A61B 8/08*       (2006.01)
      *A61B 8/00*       (2006.01)
      *G01N 29/04*      (2006.01)
      *G01N 29/06*      (2006.01)
      *G01N 29/07*      (2006.01)
      *G01N 29/46*      (2006.01)
      *G01N 29/48*      (2006.01)
      *G06T 7/00*       (2017.01)

(52) U.S. Cl.
CPC ......... *G01N 29/043* (2013.01); *G01N 29/069* (2013.01); *G01N 29/07* (2013.01); *G01N 29/46* (2013.01); *G01N 29/48* (2013.01); *G06T 7/0012* (2013.01); *G01N 2291/106* (2013.01); *G06T 2207/10132* (2013.01); *G06T 2207/20056* (2013.01); *G06T 2207/30004* (2013.01)

(56) References Cited

U.S. PATENT DOCUMENTS

2012/0111116 A1    5/2012    Minonzio et al.
2015/0212051 A1    7/2015    Bannouf et al.

OTHER PUBLICATIONS

Li, Y. et al., "Plane-wave imaging using synthetic aperture imaging reconstruction technique with regularized singular-value decomposition (RSVD)", 2016 IEEE International Ultrasonics Symposium Proceedings (IUS), IEEE, Sep. 2016, XP032988813, 3 pages.

Deylami, A. M. et al., "An improved minimum variance beamforming applied to plane-wave imaging in medical ultrasound", 2016 IEEE International Ultrasonics Symposium Proceedings (IUS), IEEE, Sep. 2016, XP032988777, 4 pages.

Tiran, E. et al., "Multiplane wave imaging increases signal-to-noise ratio in ultrafast ultrasound imaging", Institute of Physics and Engineering in Medicine, Physics in Medicine & Biology, vol. 60, No. 21, 2015, XP020290386, ISN: 0031-9155, DOI: 10/1088/0031-9155/60/21/8549, pp. 8549-8566.

Montaldo, G. et al., "Coherent Plane-Wave Compounding for Very High Frame Rate Ultrasonography and Transient Elastography", IEEE Transactions on Ultrasonics, Ferroelectrics and Frequency Control, IEEE, vol. 56, No. 3, Mar. 2009, pp. 489-506.

Prada, C. et al., "Eigenmodes of the time reversal operator: A solution to selective focusing in multiple-target media", Wave Motion 20 (1994), pp. 151-163.

Marcenko, V. A. et al., "Distribution of Eigenvalues for Some Sets of Random Matrices", Math. USSR—Sbornik, vol. 1, No. 4, 1967, pp. 457-483.

Aubry, A. et al., "Detection and imaging in a random medium: a matrix method to overcome multiple scattering and aberration", 2009 American Institute of Physics, J. Appln. Phys., vol. 106, No. 4, pp. 1-48.

Lopez Villaverde, E. et al., "Ultrasonic imaging of defects in coarse-grained steels with the decomposition of the time reversal operator", Accoustical Society of America, J. Acoust. Soc. Am., vol. 140, No. 1, Jul. 2016, pp. 541-550.

\* cited by examiner

METHOD FOR PROCESSING SIGNALS COMING FROM AN ACQUISITION BY ULTRASOUND PROBING, CORRESPONDING COMPUTER PROGRAM AND ULTRASOUND PROBING DEVICE

The present invention relates to a method for processing signals coming from an acquisition by ultrasound probing in order to carry out imaging or adaptive and selective focusing. It also relates to a corresponding computer program and ultrasound probing device.

The invention applies in particular to the field of non-destructive testing via ultrasounds, wherein the acquisition of ultrasound signals allows to detect and/or to display defects in structures, but it can also apply to any type of ultrasound echographic detection or imaging, in particular to the medical field for the inspection of zones of interest in the human or animal body.

It relates more particularly to a processing method acquiring the ultrasound signals in the following manner:
- controlling L emission transducers for M successive emissions of plane ultrasound waves having M different successive angles of emission in M emission zones,
- controlling N reception transducers in such a way as to simultaneously receive, over a predetermined time, for each emission, N measurement time signals, measuring in particular echoes caused by reflections of the emission in question,
- obtaining a matrix [MR(t)] of ultrasound time signals having a size of N×M, each coefficient $MR_{i,j}(t)$ of this matrix representing the measurement signal received by the i-th reception transducer caused by the j-th emission.

Such an acquisition is generally carried out using a probing device with a multielement sensor, wherein each transducer is both an emitter and receiver, and switching between these two modes can be controlled electronically. The sensor can be placed in contact with the object to be probed or at a distance, but in the latter case it must be submerged in order to ensure the transmission of the ultrasound waves into the object to be probed. This sensor can be linear (1D) or matrix (2D), with rigid or flexible elements.

The matrix [MR(t)] of time signals obtained by this type of acquisition, generally qualified as a matrix of the plane waves, can thus be subjected to processing, in particular for providing an image of the zone of interest inspected or for the extraction of parameters signifying structural defects in the zone of interest inspected. Given the current calculation capacities of processors, this processing can be on board in the control instruments for real-time processing.

This type of acquisition, generally qualified as "plane-wave compounding" or "plane-wave imaging", is for example described in the article by Montaldo et al, entitled "Coherent plane-wave compounding for very high frame rate ultrasonography and transient elastography", published in IEEE Transactions on Ultrasonics Ferroelectrics and Frequency Control, vol. 56, No. 3, pages 489-506, March 2009. It is substantially envisaged in the medical field and implemented in certain ultra-fast echographs allowing to image maps of the elasticity of the human body. The resulting image is of high quality and only requires several tens of ultrasound firings (generally M is between 10 and 30) for a sensor of N=128 emission/reception transducers, versus 128 firings or almost that many for other imaging techniques such as synthetic total focusing based on an acquisition of the FMC type (from "Full Matrix Capture") or equivalent. Moreover, the resulting algorithms and the associated uses are particularly well suited to a parallelization of the calculations on processors of the GPU type (from "Graphic Processing Unit") implanted in the video cards of computers. The performance of an echograph using a technique of "plane-wave compounding" can thus reach 10,000 images/s in practice. Another advantage of this acquisition technique lies in the fact that each firing is carried out by using all the emission transducers in such a way that the emission energy is high, making this method less sensitive to the phenomena of attenuation, electronic and structural noise.

This type of acquisition is also used in the patent application WO 2015/092250 A1 by astutely adapting to it the principle of synthetic total focusing, in such a way as to take advantage of the simplicity of the technique of "plane-wave compounding" with a view to reaching a high acquisition rate and image quality, in terms of spatial resolution and contrast, linked to synthesised total focusing of the desired image. This has made possible the technique of "plane-wave compounding" for uses of non-destructive testing.

But regardless of the imaging technique chosen, the images obtained via non-destructive testing can have a significant level of noise according to the properties of the medium probed. For example, this involves electronic noise when the material is homogenous and viscoelastic, or structural noise when the waves are diffused by heterogeneities in the material. The images calculated with the techniques of total focusing are also affected by artefacts, or phantom echoes, linked to geometry echoes, for example the echo of a bottom of a part near that of a defect.

It may thus be desired to design a method for processing ultrasound signals that allows to overcome at least a portion of the aforementioned problems and constraints while using the advantageous acquisition of the signals by successive emissions of plane waves.

A method for processing signals coming from an acquisition by ultrasound probing comprising the following steps is therefore proposed:
- controlling L emission transducers for M successive emissions of plane ultrasound waves having M different successive angles of emission in M emission zones,
- controlling N reception transducers in such a way as to simultaneously receive, over a predetermined time, for each emission, N measurement time signals, measuring in particular echoes caused by reflections of the emission in question, and
- obtaining a matrix [MR(t)] of ultrasound time signals having a size of N×M, each coefficient $MR_{i,j}(t)$ of this matrix representing the measurement signal received by the i-th reception transducer caused by the j-th emission, then
- transformation of the matrix [MR(t)] of time signals into a matrix [FTMR(f)] of frequency signals, then singular-value decomposition of the matrix [FTMR(f)] of frequency signals,
- elimination of a portion of the singular values and associated singular vectors resulting from said singular-value decomposition, and
- reconstruction of a denoised matrix $[MR_U(t)]$ of time signals on the basis of the singular values and singular vectors not eliminated.

Although the matrix of the plane waves [MR(t)] is not of the same nature as the matrices of inter-element impulse responses usually obtained by the conventional techniques of acquisition using synthetic total focusing, it was unexpectedly observed that a method of noise filtering based on a singular-value decomposition of a transform of the matrix of the plane waves in the frequency domain provides surprising results in terms of reduction of the noise. The denoised matrix [MR$_U$(t)] thus obtained allows in particular image reconstruction of clearly improved quality with respect to that which is produced by the matrix of the plane waves [MR(t)] without this processing.

Optionally:
the elimination of a portion of the singular values and associated singular vectors is carried out according to a predetermined criterion of distinction between singular values linked to defects and singular values linked to noise, and the reconstruction of the denoised matrix [MR$_U$(t)] of time signals comprises a reconstruction of a denoised matrix [FTMR$_U$(f)] of frequency signals on the basis of the singular values and singular vectors not eliminated, then an inverse transform of this denoised matrix [FTMR$_U$(f)] of frequency values into the denoised matrix [MR$_U$(t)] of time signals.

Also optionally, the transform and the inverse transform are discrete Fourier transforms.

Also optionally, the elimination of a portion of the singular values and associated singular vectors is carried out by:
comparison of a decrease in amplitudes of the singular values to a theoretical curve of decrease in singular values resulting from a theoretical noise matrix, the components of which are independent Gaussian random variables, then removal of the singular values belonging, give or take a common proportionality coefficient, to the theoretical decrease curve.

Also optionally, the theoretical decrease curve is defined by a reciprocal function $F^{-1}(1-\sigma)$ itself defined by a function $F(\sigma)$, called function of distribution of random singular values, such that:

$$F(\sigma) = \frac{1}{\pi}\left[\frac{\sigma}{2}\sqrt{4-\sigma^2} + 2\arcsin\left(\frac{\sigma}{2}\right)\right]\prod_{[0;2]},$$

where $\Pi_{[0;2]}$ designates the rectangular function over the interval [0;2].

Also optionally, a method for processing ultrasound signals according to the invention can further comprise a reconstruction of an imaged zone by calculation, in each point of a plurality of predetermined points of this imaged zone, of a value resulting from a coherent sum of instantaneous values respectively taken by at least a portion of the N×M time signals of the matrix [MR$_U$(t)] at times of flight respectively corresponding to a passage through the point in question according to a predetermined propagation mode.

Also optionally, the calculation is carried out on a portion of the N×M time signals of the matrix [MR$_U$(t)] in an angular sector restricted in all of the successive emissions, this restricted angular sector being selected in such a way that the plane waves that are excluded therefrom do not interact with at least one defect linked to the singular values and singular vectors not eliminated.

Also optionally, the restricted angular sector is selected on the basis of a comparison, for at least one of the singular values not eliminated, of an experimental phase value of the singular vector that is associated with it in emission to a theoretical phase value in the presence of said at least one defect linked to this singular vector.

A computer program that can be downloaded from a communication network and/or is recorded on a medium readable by computer and/or can be executed by a processor, comprising instructions for executing the steps of a method for processing ultrasound signals according to the invention, when said program is executed on a computer, is also proposed.

An ultrasound probing device is also proposed, comprising:
a probe comprising L ultrasound emission transducers and N ultrasound reception transducers, means for controlling the L emission transducers for M successive emissions of plane ultrasound waves having M different successive angles of emission in M emission zones, means for controlling the N reception transducers in such a way as to simultaneously receive, over a predetermined time, for each emission, N measurement time signals, measuring in particular echoes caused by reflections of the emission in question, and a processor for reconstructing a matrix [MR(t)] of ultrasound time signals having a size of N×M, each coefficient MR$_{i,j}$(t) of this matrix representing the measurement signal received by the i-th reception transducer caused by the j-th emission, the processor being further configured to carry out the following processing:
transformation of the matrix [MR(t)] of time signals into a matrix [FTMR(f)] of frequency signals, then singular-value decomposition of the matrix [FTMR(f)] of frequency signals, elimination of a portion of the singular values and associated singular vectors resulting from said singular-value decomposition, and reconstruction of a denoised matrix [MR$_U$(t)] of time signals on the basis of the singular values and singular vectors not eliminated.

Figure 2:
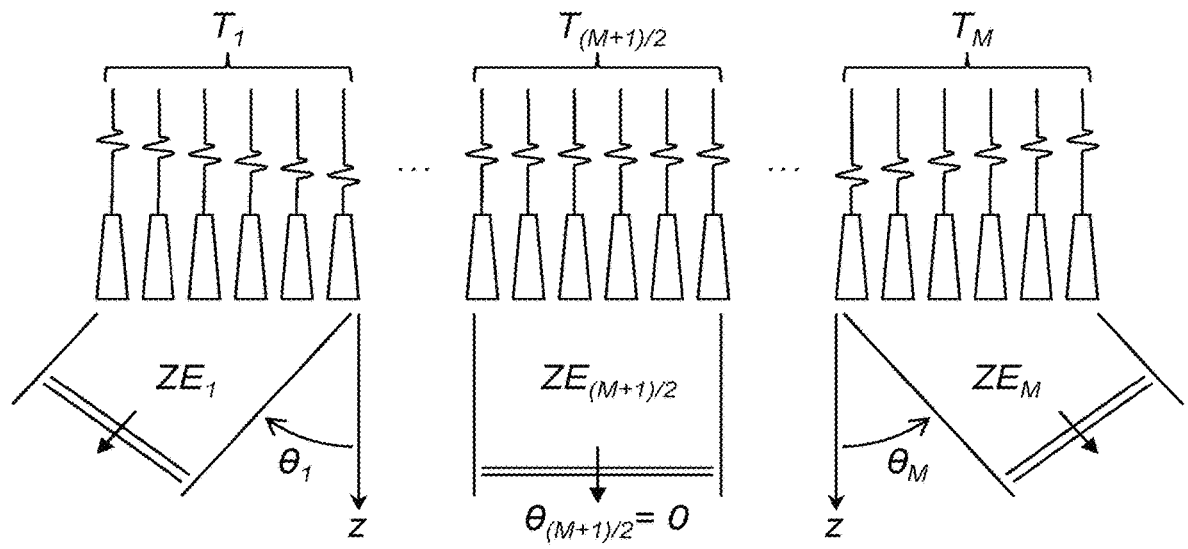
Figure 3:
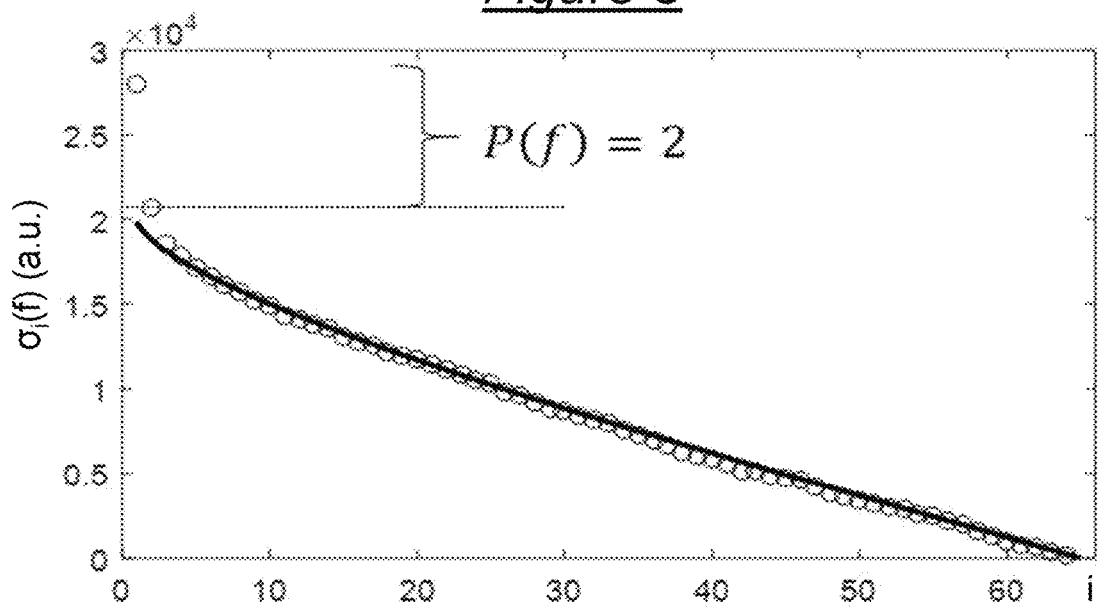
Figure 4:
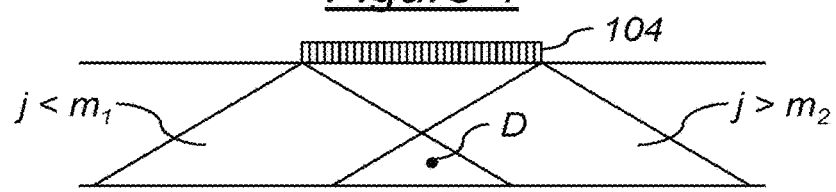
Figure 5:
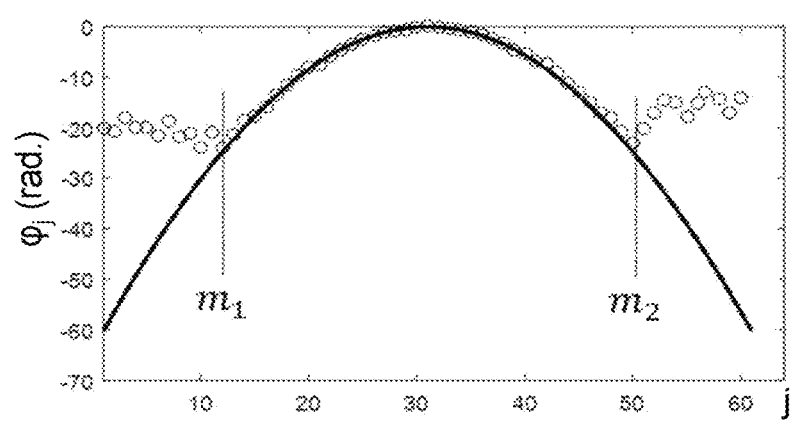
Figure 6:
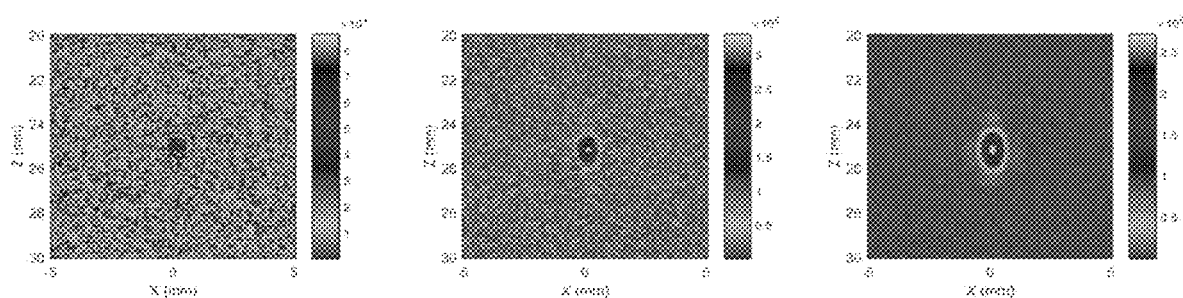
Figure 7:
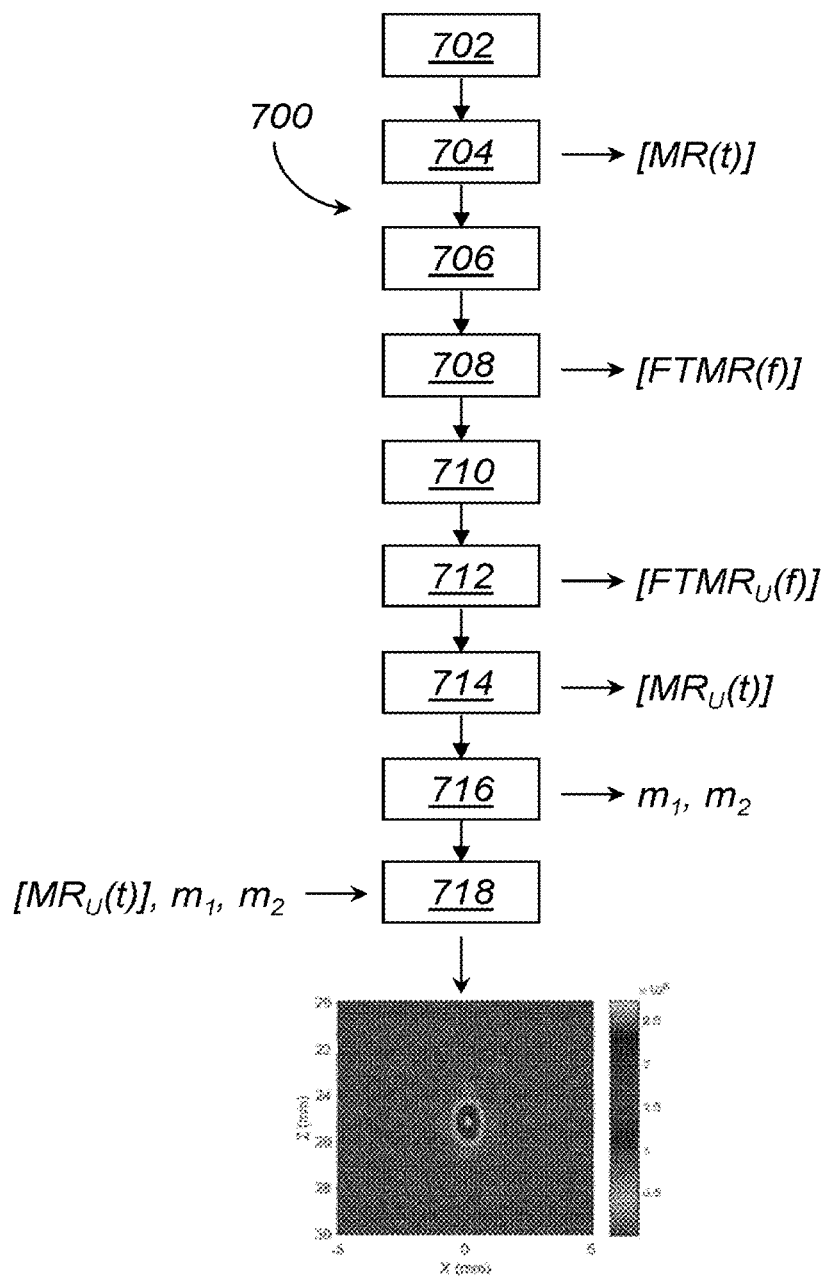

The invention will be better understood via the following description, given only as an example and made in reference to the appended drawings in which:

FIG. 1 schematically shows the overall structure of an ultrasound probing device according to an embodiment of the invention, FIG. 2 illustrates a principle of successive emissions of plane ultrasound waves implemented by the device of FIG. 1, FIG. 3 graphically illustrates the result of a singular-value decomposition of a matrix of frequency signals obtained by transformation of a matrix of plane waves itself obtained using emissions carried out according to the principle of FIG. 2, FIGS. 4 and 5 schematically and graphically illustrate the principle of a selection of a restricted angular sector in order to improve the detection of a defect, according to an embodiment of the invention, FIG. 6 illustrates three examples of images reconstructed with or without the application of the principles of the invention, and FIG. 7 illustrates the successive steps of a method for acquiring and processing ultrasound signals implemented by the device of FIG. 1, according to an embodiment of the invention.

In reference to FIG. 1, a device 100 for probing an object 102 according to an embodiment of the invention comprises an ultrasound probe 104 having a case 106, that is to say a non-deformable structural element that is used as a reference frame attached to the probe 104, in which are disposed, for example linearly or in a matrix, N fixed or mobile transducers $108_1, \ldots, 108_N$ arranged in a network.

The object 102 is for example a mechanical part that it is desired to examine via non-destructive testing or, in a medical context, a human or animal body part that it is desired to inspect non-invasively. In the embodiment of FIG. 1, the object 102 is submerged in a liquid, such as water 110, and the probe 104 is maintained at a distance from the object 102 in order to the water 110 to separate them. But in another equivalent embodiment, the probe 104 could be in direct contact with the object 102.

The transducers $108_1, \ldots, 108_N$ are designed to individually emit ultrasound waves in the direction of the object 102 in response to control signals identified by the general reference C, in main directions parallel to each other, indicated by dotted arrows in FIG. 1, and in a main plane that is that of the drawing.

The transducers $108_1, \ldots, 108_N$ are further designed to detect echoes of the ultrasound waves reflecting on and in the object 102 and to provide measurement signals identified by the general reference S and corresponding to these echoes. Thus, in the non-limiting example of FIG. 1, the transducers $108_1, \ldots, 108_N$ carry out the functions of both emission and reception, but receivers different than the emitters could also be provided in different and independent cases while remaining in conformity with the principles of the invention. Moreover, the number L of emitters could indeed be different than the number N of receivers.

The probing device 100 further comprises an electronic circuit 112 for control of the transducers $108_1, \ldots, 108_N$ of the probe 104 and for processing of the measurement signals S. This electronic circuit 112 is connected to the probe 104 in order to transmit to it the control signals C and in order to receive the measurement signals S. The electronic circuit 112 is for example that of a computer. It has a central processing unit 114, such as a microprocessor designed to emit, to the probe 104, the control signals C and to receive, from the probe 104, the measurement signals S, and a memory 116 in which a computer program 118 is in particular recorded.

The computer program 118 comprises first of all instructions 120 for generating the signals C for control of the transducers $108_1, \ldots, 108_N$ and receiving their echoes. These instructions are more precisely programmed in such a way as to:

activate the L=N transducers $108_1, \ldots, 108_N$ as emitters for M successive emissions of plane ultrasound waves having M different successive angles of emission in M emission zones of the object 102, activate the transducers $108_1, \ldots, 108_N$ as receivers in order to, after each emission, simultaneously receive, by these N receivers and for a predetermined time of the desired depth of inspection, N measurement time signals, measuring in particular echoes caused by reflections of each emission in question.

The plane ultrasound waves are obtained at emission by applying, to the transducers $108_1, \ldots, 108_N$, delay laws recorded in a memory 116 in a database 122 of delay laws. Each delay law defines delays to be applied to the emission transducers $108_1, \ldots, 108_N$, in such a way as to generate a plane ultrasound wave at a desired angle of emission out of the M different successive angles of emission. There are therefore as many delay laws as desired successive emissions.

As illustrated in FIG. 2 in the case in which the number M of successive emissions is odd and in which the angles of emissions succeed each other with a constant increment in an angular sector symmetrical with respect to the direction z orthogonal to the network of transducers $108_1, \ldots, 108_N$, the first plane-wave emission is associated with a delay law $T_1$ relating to signals emitted by the transducers $108_1, \ldots, 108_N$, allowing the emission of a plane wave having an angle of emission $\theta_1$ with respect to the direction z in a first emission zone $ZE_1$ partly located outside of the opening of the probe 104. The (M+1)/2-th plane-wave emission is associated with a uniform delay law $T_{(M+1)/2}$ for the emission of a plane wave having an angle of emission of zero with respect to the direction z in an (M+1)/2-th emission zone $ZE_{(M+1)/2}$ covering the opening of the probe 104. Finally, the last plane-wave emission is associated with a delay law $T_M$ allowing the emission of a plane wave having an angle of emission of $\theta_M = -\theta_1$ with respect to the direction z in a last emission zone $ZE_M$ partly located outside of the opening of the probe 104. In general, the j-th plane-wave emission is associated with a delay law $T_j$ allowing the emission of a plane wave having an angle of emission of $\theta_j = \theta_1 + (j-1) \cdot (\theta_M - \theta_1)/(M-1)$ with respect to the direction z. In reality, most often M is even: there is therefore no emission at 0° and the angular increment is not constant.

Given the acquisition technique used, the zone to be imaged must be contained in the union of the M zones of successive emissions. As a result, this zone can extend beyond the opening of the probe 104, as is visible in FIG. 2. In particular, the imaged zone can take the shape of a sectoral zone defined by the ends of the emission zones having a maximum and minimum angle. An image of the S-scan type can thus be obtained.

Alternatively, and as advantageously made possible by the principle of acquisition of the signals via successive emissions of plane waves, the M different successive emission angles $\theta_1$ to $\theta_M$ can be defined around an average direction $\theta_{(M+1)/2}$ not perpendicular to the network of transducers $108_1, \ldots, 108_N$. In particular, when defects such as a crack disposed at the bottom of an object to be inspected via non-destructive inspection are to be detected, this crack further being perpendicular to the network of transducers, it is preferable to laterally offset the zone to be inspected with respect to the probe 104 and to emit around an average of 45° for example. The zone to be inspected can even be offset to the point of completely exiting the opening of the probe 104.

In order to improve the quality of the measurement signals used to reconstruct the imaged zone, it is moreover possible to apply an apodisation of the ultrasound signals emitted by the transducers $108_1, \ldots, 108_N$ in order to form a plane ultrasound wave of better quality, without distortion undergone because of the effects of edges. Such an apodisation is carried out at each emission spatially on all of the transducers using an apodisation window such as a trapezoidal, Hamming or Blackman-Harris amplitude rule. The result thereof is to provide a better definition of the successive emission zones.

Again in reference to FIG. 1, upon reception of the signals resulting from each of the M successive emissions, the set S of the N×M measurement time signals received by the N transducers $108_1, \ldots, 108_N$ is sent back by the probe 104 to the central processing unit 114.

The computer program 118 thus further comprises instructions 124 for constructing a matrix [MR(t)] of ultrasound time signals having a size of N×M, qualified as a matrix of the plane waves. Each coefficient $MR_{i,j}(t)$ of this matrix represents the measurement signal received by the transducer $108_i$ in response to the j-th emission.

Optionally, the computer program 118 further comprises instructions 126 for carrying out temporal filtering of the matrix [MR(t)], this filtering aiming to remove any information located at times of flight excluded from the zone of interest in the object 102.

The computer program 118 further comprises instructions 128 for transforming the matrix [MR(t)] into a matrix [FTMR(f)] of frequency signals via a Fourier transform, advantageously via a discrete Fourier transform after time sampling of the ultrasound signals forming the coefficients of the matrix [MR(t)], or, even more advantageously, by calculation of FFT (from "Fast Fourier Transform") if the number of samples of each coefficient of the matrix [MR(t)] allows it.

The computer program 118 further comprises instructions 130 for decomposing the matrix [FTMR(f)] of frequency signals into singular values over a frequency band. Although it is known to singular-value decompose a matrix of interelement impulse responses usually obtained by the conventional acquisition techniques using synthetic total focusing, this operation is not equivalent when it is applied to a matrix such as the matrix [FTMR(f)]. Indeed, the matrix noted as [PFTMR(f)] having dimensions of M×M and defined by the product [FTMR(f)]$^\dagger$·[FTMR(f)], where "\" is the symbol of the conjugate transpose of a matrix, does not represent the time-reversal operator in emission like for the matrix of the inter-element impulse responses. The physical interpretation of the singular values and singular vectors is not therefore the same as in the method of Decomposition of the Time-Reversal Operator (DORT method, from French "Décomposition de l'Opérateur de Retournement Temporel") as taught in the article by Prada et al, entitled "Eigenmodes of the time reversal operator: a solution to selective multiple-target media", published in Wave Motion 20, pages 151-163 (1994). Moreover, the matrix [FTMR(f)] is not generally square nor symmetrical, M often being even markedly less than N in acquisition by emission of plane waves. Thus, a singular-value decomposition does not produce diagonalisation like in most of the works relating to the matrix of the inter-element impulse responses.

More precisely, the operation of singular-value decomposition allows to estimate the matrices U(f), S(f) and V(f) such that:

$$[FTMR(f)] = U(F) \cdot S(f) \cdot V^\dagger(f) = \sum_{i=1}^{K} \sigma_i(f) \cdot u_i(f) \cdot v_i^\dagger(f),$$

where $U(f) = [\mu_1(f), \ldots, u_N(f)]$ and V=[$v_1$(f), . . . , $v_M$(f)] are orthogonal unitary matrices having respective sizes of N×N and M×M, which respectively contain the singular vectors during reception and emission, where S is a real matrix having a size of N×M containing the K=min(N;M) singular values $\sigma_i$(f) of the matrix [FTMR(f)], in decreasing order at a given frequency f $\sigma_1$(f)≥ . . . ≥$\sigma_K$(f)≥0, and where min(N;M) is the function that returns the minimal value between N and M (generally, this is M).

The computer program 118 further comprises instructions 132 for reducing the rank of the matrix [FTMR(f)], by eliminating a portion of the singular values $\sigma_i$(f). This elimination is carried out according to a criterion for distinction between singular values linked to defects and singular values linked to noise, the former having amplitudes greater than the latter. Given the fact that $\sigma_1$(f)≥ . . . ≥$\sigma_K$(f)≥0, this involves finding the integer value P(f) between 1 and K such that $\sigma_1$(f), . . . , $\sigma_{P(f)}$(f) can be considered to be linked to defects to be detected in the object 102 and $\sigma_{P(f)+1}$(f), . . . , $\sigma_K$(f) can be eliminated since they are considered to be linked to noise. In the case of small defects ideally spaced apart from each other, P(f) is equal to the number of defects present in the zone of interest inspected. The matrix [FTMR(f)] can thus be written in the form of a sum of two matrices [FTMR$_U$(f)] and [FTMR$_N$(f)]:

[FTMR(f)]=[FTMR$_U$(f)]+[FTMR$_N$(f)], with $$[FTMR_U(f)] = \sum_{i=1}^{P(f)} \sigma_i(f) \cdot u_i(f) \cdot v_i^\dagger(f),$$

called useful-signal matrix, and $$[FTMR_N(f)] = \sum_{i=P(f)+1}^{K} \sigma_i(f) \cdot u_i(f) \cdot v_i^\dagger(f),$$

called noise matrix.

Reducing the rank of the matrix [FTMR(f)] thus means only keeping [FTMR$_U$(f)].

In practice, the determination of P(f) is carried out by a study of the curve of decrease in the amplitudes of the singular values. This study can be carried out on the basis of the theory of random matrices as taught in:

the article by Marčenko et al, entitled "Distribution of eigenvalues for some sets of random matrices", published in Mathematics of the USSR-Sbornik, vol. 1, No. 4, pages 457-483 (1967), and the article by Aubry et al, entitled "Detection and imaging in a random medium: a matrix method to overcome multiple scattering and aberration", published in Journal of Applied Physics, 106(4), 044903 (2009).

By supposing that all the components of the noise matrix [FTMR$_N$(f)] are independent Gaussian random variables, it can indeed be demonstrated that the singular values related to the noise $\sigma_{P(f)+1}$(f), . . . , $\sigma_K$(f) belong, give or take a common proportionality coefficient, to the theoretical curve defined by a reciprocal function $F^{-1}(1-\sigma)$ itself defined by a function F($\sigma$), called function of distribution of random singular values, with:

$$F(\sigma) = \frac{1}{\pi}\left[\frac{\sigma}{2}\sqrt{4-\sigma^2} + 2\arcsin\left(\frac{\sigma}{2}\right)\right]\prod_{[0;2]},$$

where $\Pi_{[0;2]}$ designates the rectangular function over the interval [0;2].

The function F($\sigma$) gives values between 0 and 1 over the support interval $\sigma \in [0;2]$, where $\sigma$ is the variable having a singular value. Moreover, it is strictly increasing. Its reciprocal function $F^{-1}(\sigma)$ is thus also strictly increasing, in such a way that the function $F^{-1}(1-\sigma)$ gives the desired curve of decrease in the singular values, give or take a proportionality constant for adjusting it to the experimental curve.

Thus, the number of singular values calculated by execution of the instructions 130 not belonging to this theoretical curve defines the rank P(f) of the useful-signal matrix [FTMR$_U$(f)]. For example, FIG. 3 illustrates, in arbitrary units a.u., a distribution of singular values calculated at a frequency f=5 MHz, for an acquisition carried out with a sample of polyethylene by emitting M=64 plane waves between −31.5° and +31.5°. Two singular values deviate from the theoretical curve, one of which rather markedly, indicating in this example that P(f)=2 to 5 MHz.

In order to calculate the useful-signal matrix [FTMR$_U$(f)] over a plurality of frequencies f, it suffices to identify, at each desired frequency, the number of singular values not belonging to the theoretical curve.

The matrix [FTMR$_U$(f)] thus reconstructed is a denoised matrix of frequency signals, the noise subspace represented by the matrix [FTMR$_N$(f)] having been eliminated.

The computer program 118 further comprises instructions 134 for transforming the matrix [FTMR$_U$(f)] into a denoised matrix [MR$_U$(t)] of time signals via an inverse Fourier transform, advantageously via an inverse discrete Fourier transform, or, even more advantageously, by calculation of IFFT (from "Inverse Fast Fourier Transform") if the number of samples of each coefficient of the matrix [FTMR$_U$(f)] allows it.

Finally, the computer program 118 comprises instructions, designated by the general reference 136, for processing the matrix [MR$_U$(t)]. The processing carried out by the instructions 136 can include a reconstruction of a digital image of the zone of interest in the object 102 by adaptation of the principle of synthetic total focusing, as taught for example in the document WO 2015/092250 A1. A digital image of the zone of interest, the quality of which is better than if the reconstruction had been carried out on the non-denoised matrix [MR(t)], is thus reconstructed. In particular, the Signal-to-Noise Ratio (SNR) is improved. Alternatively or in addition, the processing carried out by the instructions 136 could include adaptive and selective focusing.

According to a relatively simple but not always optimal adaptation of the synthetic total focusing, in each pixel P of the reconstructed digital image, the modulus A(P) of a coherent sum involving the N×M time signals of the matrix [MR$_U$(t)] at N×M times of flight calculated according to a predetermined propagation mode is calculated, each time of flight $t_{i,j}$ being the time it takes for the j-th plane wave to be received by the i-th reception transducer when passing through the pixel in question according to the predetermined propagation mode:

$$A(P)=|\Sigma_{j=1}^{M}\Sigma_{i=1}^{N}\mu_j(P)\rho_i(P)MR_{U_{i,j}}[t_{i,j}(P)]|,$$

where $\mu_j(P)$ and $\rho_i(P)$ are weighting coefficients respectively in emission and in reception, the expressions of which depend on the use in question in order to take into account phenomena or processing such as filtering of geometry echoes, compensation for attenuation caused by a spatial spreading out of the waves, etc.

This calculation mode often is not optimal because, as illustrated by FIG. 4, all the plane waves emitted by the probe 104 do not interact with the defect(s) D linked to the singular values of the useful-signal matrix [FTMR$_U$(f)], that is to say the singular values $\sigma_1(f), \ldots, \sigma_{P(f)}(f)$. It can thus be advantageous to select a restricted angular sector $[\theta_{m1}; \theta_{m2}]$ in the set of the successive emissions outside of which the plane waves do not interact with the aforementioned defect(s). This restricted angular sector is defined by its minimum ($m_1$) and maximum ($m_2$) index of emissions where $1 \leq m_1 \leq m_2 \leq M$. The modulus A(P) is thus preferably calculated by the following coherent sum:

$$A(P)=|\Sigma_{j=m_1}^{m_2}\Sigma_{i=1}^{N}\mu_j(P)\rho_i(P)MR_{U_{i,j}}[t_{i,j}(P)]|.$$

In the case of a defect that can be likened to a punctual reflector, an ingenious method for determining the values of $m_1$ and $m_2$ will now be described in detail in reference to FIG. 5. It consists of comparing, for at least one of the singular values $\sigma_1(f), \ldots, \sigma_{P(f)}(f)$, and in particular at least for the first singular value $\sigma_1(f)$ that is the greatest, an experimental phase value of the singular vector that is associated with it in emission to a theoretical phase value in the presence of the defect(s) D. This comparison is carried out at a chosen frequency $f_c$ that can be the central operating frequency of the probe 104, a frequency for which the singular value $\sigma_1(f)$ takes its greatest value, or any other predetermined frequency. In FIG. 5, the comparison is thus carried out at 5 MHz for the emission singular vector $v_1(f)$ corresponding to a location of defect(s) D having the coordinates $(X_D, Z_D)$.

In the experimental conditions indicated above, the theoretical phase value is a corrected phase calculated in the following manner in order to always be negative:

$$\forall j, 1 \leq j \leq M,$$

$$\varphi_j^{th} = \frac{2\pi f_c(X_D \sin\theta_j + Z_D \cos\theta_j)}{c} - \max_{1 \leq j \leq M}\left[\frac{2\pi f_c(X_D \sin\theta_j + Z_D \cos\theta_j)}{c}\right],$$

with c the velocity of the plane wave in the medium in question and $\theta_j$ its angle of emission.

The coordinates $(X_D, Z_D)$ can be determined with the useful-signal matrix [FTMR$_U$(f)] by calculating the back-propagation of the reception singular vector $u_1(f)$ at the frequency $f_c$, for example as taught in the article by Lopez Villaverde et al, entitled "Ultrasonic imaging of defects in coarse-grained steels with the decomposition of the time reversal operator", published in Journal of the Acoustical Society of America, volume 140, No. 1, pages 541-550 (2016).

The above definition of the corrected theoretical phase gives the curve shown as a solid line in FIG. 5.

The experimental phase value of the emission singular vector $v_1(f_c)$ is also a corrected phase calculated in the following manner in order to always be negative:

$$\forall j, 1 \leq M, \varphi_j^{v_1(f_c)} = \arg[v_{1(f_c)}]_j - \max_{1 \leq j \leq M}\left[\arg[v_{1(f_c)}]_j\right].$$

This definition of the corrected phase of the singular vector $v_1(f_c)$ gives the M values shown by small circles in FIG. 5.

It is observed that the experimental and theoretical values correspond well inside a restricted angular sector, the ends of which give the values of $m_1$ and $m_2$. Outside of this restricted angular sector, the experimental values deviate very markedly from the theoretical values.

In general, if the comparison is carried out for a plurality of singular values linked to the defect(s) D, the values finally retained for $m_1$ and $m_2$ can respectively be the minimum and the maximum of the values found for each of the singular values of the useful-signal matrix.

The advantageous calculation mode described in detail above can also be combined with an adaptation of the principle of synthetic total focusing as taught in the document WO 2015/092250 A1.

FIG. 6 illustrates, in an example of a probed object comprising a central circular defect D, three images obtained:

by an FMC acquisition with reconstruction of the image by synthetic total focusing (image on the left), by an acquisition and processing as taught in the document WO 2015/092250 A1 (image in the centre), and by an acquisition and processing of filtering and selection of a restricted angular sector as taught according to the principles of the present invention (image on the right).

A strong reduction of the noise (gain of 20 dB in particular between the image in the centre and that on the right in terms of SNR) and better visibility of the defect are observed.

In reference to FIG. 7, an example of a method 700 for acquisition and processing of ultrasound signals that the device 100 of FIG. 1 can implement will now be described according to a preferred embodiment of the invention.

During a step 702, the processing unit 114 executing the instructions 120 controls the sequences of emissions and of receptions of the transducers $108_1, \ldots, 108_N$ for the acquisition of the measurement signals $MR_{i,j}(t)$ of the matrix [MR(t)].

There is a number M, an integer that can be much lower than the number N of transducers $108_1, \ldots, 108_N$, of these sequences. After each firing, the signals are received on all of the N transducers, digitized and transmitted to the electronic circuit 112.

During a step 704, the processing unit 114 executing instructions 124 records the measurement signals $MR_{i,j}(t)$, these signals being digitised in order to facilitate their later processing. The steps 702 and 704 can be executed simultaneously, that is to say that it is not necessary to wait for all the firings to be carried out in order to start recording the measurement signals and carrying out processing such as image reconstruction.

During an optional step 706, the processing unit 114 executing the instructions 126 carries out temporal filtering of the matrix [MR(t)], this filtering aiming to remove any information located at times of flight excluded from the zone of interest. The goal of this step 706 is to then facilitate the separation of the two subspaces represented by the matrices $[FTMR_U(f)]$ and $[FTMR_N(f)]$, in particular when the defects to be imaged are close to a strongly echogenic interface, like a bottom of a part. It allows to limit the zone to be imaged to the close vicinity of the defects by excluding in particular the disturbing echogenic interfaces. It is very advantageous in the imaging of cracks forming from the bottom of the object.

During a step 708, the processing unit 114 executing the instructions 128 carries out a discrete Fourier transform of the matrix [MR(t)] in order to obtain the matrix [FTMR(f)] of frequency signals.

During a step 710, the processing unit 114 executing the instructions 130 carries out a singular-value decomposition of the matrix [FTMR(f)], as described in detail above.

During a step 712, the processing unit 114 executing the instructions 132 reduces the rank of the matrix [FTMR(f)] by only keeping the useful-signal matrix $[FTMR_U(f)]$.

During a step 714, the processing unit 114 executing the instructions 134 carries out a discrete inverse Fourier transform of the matrix $[FTMR_U(f)]$ in order to obtain the denoised matrix $[MR_U(t)]$ of time signals.

During a step 716, the processing unit 114 executing the instructions 136 selects, optionally but advantageously, an angular sector restricted in all of the successive emissions, outside of which the plane waves do not interact with the defect(s) to be detected. This restricted angular sector is defined by its minimum ($m_1$) and maximum ($m_2$) index of emissions for example according to the method described in detail above.

Finally, during a last step 718, the processing unit 114 still executing the instructions 136 reconstructs and displays a digital image of the effective zone of interest by adaptation of the principle of synthetic total focusing on the basis of the denoised matrix $[MR_U(t)]$ in the restricted angular sector selected.

It is clear that an ultrasound probing device such as that described above allows to obtain a detection of defect(s) that is denoised and of very good quality, better than those obtained by the FMC acquisitions with reconstructions of images via synthetic total focusing or by the processing as taught in the document the document WO 2015/092250 A1. Moreover, the teaching of the present patent application can be advantageously combined with that of the document WO 2015/092250 A1.

Moreover, it is noted that the invention is not limited to the embodiment described above. Indeed, it is clear to a person skilled in the art that various modifications can be made to the embodiment described above, in light of the teaching that has just been disclosed to them.

In particular, the computer program instructions could be replaced by electronic circuits dedicated to the functions carried out during the execution of these instructions.

In general, in the following claims, the terms used must not be interpreted as limiting the claims to the embodiment disclosed in the present description, but must be interpreted to include all the equivalents that the claims aim to cover by their wording and the providing of which is within the reach of a person skilled in the art by applying their general knowledge to the implementation of the teaching that has just been disclosed thereto.

The invention claimed is:

1. A method for processing signals (S) coming from an acquisition by ultrasound probing comprising the following steps:

controlling L emission transducers for M successive emissions of plane ultrasound waves having M different successive angles of emission ($\theta_1, \ldots, \theta_M$) in M emission zones ($ZE_1, \ldots, ZE_M$), controlling N reception transducers in such a way as to simultaneously receive, over a predetermined time, for each emission, N measurement time signals measuring echoes caused by reflections of the each emission, obtaining a matrix [MR(t)] of ultrasound time signals having a size of N×M, each coefficient $MR_{i,j}(t)$ of this matrix representing the measurement signal received by the i-th reception transducer caused by the j-th emission, transforming the matrix [MR(t)] of time signals into a matrix [FTMR(f)] of frequency signals, performing singular-value decomposition of the matrix [FTMR(f)] of frequency signals, eliminating a portion of the singular values and associated singular vectors resulting from said singular-value decomposition, and reconstructing a denoised matrix $[MR_U(t)]$ of time signals on the basis of the singular values and singular vectors not eliminated.

2. The method for processing ultrasound signals (S) according to claim 1, wherein:

eliminating the portion of the singular values and associated singular vectors is carried out according to a predetermined criterion of distinction between singular values linked to defects and singular values linked to noise, and reconstructing the denoised matrix $[MR_U(t)]$ of time signals comprises reconstructing a denoised matrix

[FTMR$_{t'}$(f)] of frequency signals based on the singular values and singular vectors not eliminated, then inverse transforming the denoised matrix [FTMR$_{t'}$(f)] of frequency values into the denoised matrix [MR$_{t'}$(t)] of time signals.

3. The method for processing ultrasound signals (S) according to claim 2, wherein the transforming and the inverse transforming are discrete Fourier transforms.

4. The method for processing ultrasound signals (S) according to claim 2, wherein eliminating the portion of the singular values and associated singular vectors comprises:
  comparing a decrease in amplitudes of the singular values to a theoretical curve of decrease in singular values resulting from a theoretical noise matrix, the components of which are independent Gaussian random variables, then
  removing the singular values belonging, give or take a common proportionality coefficient, to the theoretical decrease curve.

5. The method for processing ultrasound signals (S) according to claim 4, wherein the theoretical decrease curve is defined by a reciprocal function $F^{-1}(1-\sigma)$ that is defined by a function $F(\sigma)$ of distribution of random singular values, such that:

$$F(\sigma) = \frac{1}{\pi}\left[\frac{\sigma}{2}\sqrt{4-\sigma^2} + 2\arcsin\left(\frac{\sigma}{2}\right)\right]\prod\nolimits_{[0;2]},$$

where $\Pi_{[0;2]}$ designates a rectangular function over the interval [0;2].

6. The method for processing ultrasound signals (S) according to claim 1, further comprising
  reconstructing an imaged zone by calculating, in each point of a plurality of predetermined points of this imaged zone, a value resulting from a coherent sum of instantaneous values respectively taken by at least a portion of the N×M time signals of the matrix [MR$_{t'}$(t)] at times of flight respectively corresponding to a passage through the point in question according to a predetermined propagation mode.

7. The method for processing ultrasound signals (S) according to claim 6, wherein the calculating is carried out on a portion of the N×M time signals of the matrix [MR$_{t'}$(t)] in an angular sector ($m_1$, $m_2$) restricted in all of the successive emissions.

8. The method for processing ultrasound signals (S) according to claim 7, wherein the restricted angular sector ($m_1$, $m_2$) is selected based on a comparison, for at least one of the singular values not eliminated, of an experimental phase value of the singular vector that is associated with it in emission to a theoretical phase value in the presence of said at least one defect linked to the singular vector, in such a way that the plane waves that are excluded therefrom do not interact with at least one defect linked to the singular values and singular vectors not eliminated.

9. A non-transitory medium readable by computer including computer instructions for executing the steps of the method for processing ultrasound signals (S) according to claim 1, when said computer instructions are executed by a computer processor.

10. An ultrasound probing device comprising:
  a probe comprising L ultrasound emission transducers and N ultrasound reception transducers,
  means for controlling the L emission transducers for M successive emissions of plane ultrasound waves having M different successive angles of emission ($\theta_1, \ldots, \theta_M$) in M emission zones ($ZE_1, \ldots, ZE_M$),
  means for controlling the N reception transducers in such a way as to simultaneously receive, over a predetermined time, for each emission, N measurement time signals measuring echoes caused by reflections of the each emission, and
  a processor configured to
    reconstruct a matrix [MR(t)] of ultrasound time signals having a size of N×M, each coefficient MR$_{i,j}$(t) of this matrix representing the measurement signal received by the i-th reception transducer caused by the j-th emission,
    transform the matrix [MR(t)] of time signals into a matrix [FTMR(f)] of frequency signals,
    perform singular-value decomposition of the matrix [FTMR(f)] of frequency signals
    eliminate a portion of the singular values and associated singular vectors resulting from said singular-value decomposition, and
    reconstruct a denoised matrix [MR$_{t'}$(t)] of time signals on the basis of the singular values and singular vectors not eliminated.

11. An ultrasound probing device comprising:
  a probe comprising L ultrasound emission transducers and N ultrasound reception transducers, wherein the L emission transducers emit M successive emissions of plane ultrasound waves having M different successive angles of emission ($\theta_1, \ldots, \theta_M$) in M emission zones ($ZE_1, \ldots, ZE_M$) and the N reception transducers simultaneously receive, over a predetermined time, for each emission, N measurement time signals measuring echoes caused by reflections of the each emission, and
  a processor configured to
    reconstruct a matrix [MR(t)] of ultrasound time signals having a size of N×M, each coefficient MR$_{i,j}$(t) of this matrix representing the measurement signal received by the i-th reception transducer caused by the j-th emission,
    transform the matrix [MR(t)] of time signals into a matrix [FTMR(f)] of frequency signals,
    perform singular-value decomposition of the matrix [FTMR(t)] of frequency signals
    eliminate a portion of the singular values and associated singular vectors resulting from said singular-value decomposition, and
    reconstruct a denoised matrix [MR$_{t'}$(t)] of time signals on the basis of the singular values and singular vectors not eliminated.

* * * * *